US008628964B2

(12) United States Patent
Lelkes et al.

(10) Patent No.: US 8,628,964 B2
(45) Date of Patent: Jan. 14, 2014

(54) FETAL PULMONARY CELLS AND USES THEREOF

(75) Inventors: Peter I. Lelkes, Cherry Hill, NJ (US); Mark J. Mondrinos, Landsdowne, PA (US); Christine M. Finck, Glastonbury, CT (US)

(73) Assignee: Drexel University, Philadelphia, PA (US)

( * ) Notice: Subject to any disclaimer, the term of this patent is extended or adjusted under 35 U.S.C. 154(b) by 1330 days.

(21) Appl. No.: 11/870,723

(22) Filed: Oct. 11, 2007

(65) Prior Publication Data

US 2008/0112890 A1 May 15, 2008

Related U.S. Application Data

(60) Provisional application No. 60/581,093, filed on Oct. 11, 2006.

(51) Int. Cl.
*C12N 5/00* (2006.01)
*A61L 15/16* (2006.01)
*A61K 9/14* (2006.01)
*C12N 11/08* (2006.01)

(52) U.S. Cl.
USPC ............ 435/395; 424/444; 424/486; 435/180

(58) Field of Classification Search
USPC .................... 435/395, 180; 424/423, 444, 486
See application file for complete search history.

(56) References Cited

U.S. PATENT DOCUMENTS

| 6,790,455 | B2 * | 9/2004 | Chu et al. ...................... 424/423 |
| 2005/0282148 | A1 * | 12/2005 | Warren et al. ...................... 435/4 |
| 2008/0219957 | A1 * | 9/2008 | Lim et al. ...................... 424/93.7 |
| 2009/0232777 | A1 * | 9/2009 | Lundgren-Akerlund et al. ............................ 424/93.7 |

OTHER PUBLICATIONS

Shannon et al., Epithelial-Mesenchymal Interactions in the Developing Lung Annual Review of Physiology, Mar. 2004, vol. 66, pp. 625-645.*
Leinwand et al., "Nitrofen inhibition of pulmonary growth and development occurs in the early embryonic mouse", J. Pediatr. Surg. 2002 37:1263-1268.
Pollok et al., "Tissue engineering", Semin. Pediatr. Surg. 1996 5:191-196.
Kim et al., "The current status of tissue engineering as potential therapy", Semin. Pediatr. Surg. 1999 8:119-123.
Nerem, R.M., "Tissue engineering:confronting the transplantation crisis", Proc. Instn. Mech. Engrs. 2000 214 Part H:95-99.
Stock et al., "Tissue engineering:current status and prospects", Annu. Rev. Med. 2001 52:443-451.
Fuchs et al., "Tissue engineering:a 21st century solution to surgical reconstruction", Ann. Thorac. Surg. 2001 72(2):577-591.
Nerem, R.M., "Cellular engineering", Annals of Biomedical Engineering 1991 19:529-545.
Douglas et al., "The formation of histotypic structures from monodisperse fetal rat lung cells cultured on a three-dimensional substrate[1]", in Vitro 1976 12(5):373-381.
Douglas et al., "An organotypic in vitro model system for studying pulmonary surfactant production by type II alveolar pneumonocytes", Am Rev Respir Dis 1976 113:17-23.
Nakamura et al., "Mechanical strain and dexamethasone selectively increase surfactant protein C and tropoelastin gene expression", Am. J. Physiol. Lung Cell Mol. Physiol. 2000 278:L974-L980.
Paszek et al., "Tensional homeostasis and the malignant phenotype", Cancer Cell 2005 8:241-254.
Schwarz et al., "Epithelial-Mesenchymal interactions are linked to neovascularization", Am. J. Respir. Cell Mol. Biol. 2004 30:784-792.
Geppert et al., "Primary culture of rat alveolar type II cells on floating collagen membranes", Exp Cell Res 1980 128:363-374.
Blau et al., "Fetal type 2 pneumocytes form alveolar-like structures and maintain long-term differentiation on extracellular matrix", J. Cell Physiol. 1988 136:203-214.
Sugihara et al., "Reconstruction of alveolus-like structure from alveolar type II epithelial cells in three-dimensional collagen gel matrix culture", Am. J. Pathol. 1993 142(3):783-792.
Schuger et al., Laminin and haparan sulfate proteoglycan mediate epithelial cell polarization in organotypic cultures of embryonic lung cells:evidence implicating involvement of the inner globular region of laminin β 1 chain and the heparan sulfate groups of heparan sulfate proteoglycan, Dev. Biol. 1996 179:264-273.
Isakson et al., "Modulation of pulmonary alveolar type II cell phenotype and communication by extracellular matrix and KGF", Am. J. Physiol. Cell Physiol. 2001 281:C1291-C1299.
Olsen et al., "Extracellular matrix-driven alveolar epithelial cell differentiation in vitro", Exp Lung Res 2005 31:461-482.
Shannon et al., "Lung fibroblasts improve differentiation of rat type II cells in primary culture", Am. J. Respir. Cell Mol. Biol. 2001 24:235-244.
Griffin et al., "Alveolar type II cell-fibroblast interactions, synthesis and secretion of surfactant and type I collagen", Journal Cell Science 1993 105:423-432.
Linge et al., "A method for removal of fibroblasts from human tissue culture systems", Experimental Cell Research 1989 185:519-528.
Shannon et al., "Epithelial-mesenchymal interactions in the developing lung", Annu. Rev. Physiol. 2004 66:625-645.
White et al., "FGF9 and SHH signaling coordinate lung growth and development through regulation of distinct mesenchymal domains", Development 2006 133:1507-1517.
Zhang et al., "Reciprocal epithelial-mesenchymal FGF signaling is required for cecal development", Development 2006 133:173-180.

(Continued)

*Primary Examiner* — Maria Leavitt
(74) *Attorney, Agent, or Firm* — Saul Ewing LLP; Kathryn Doyle

(57) ABSTRACT

Isolated mixed populations of fetal pulmonary cells, engineered three-dimensional tissue constructs of these cells, and uses thereof in identifying therapeutic agents which augment, repair, and/or replace dysfunctional native lung and to perform in vitro studies such as pharmaceutical screening, models for lung development and disease and characterization of chemical or mechanical injury are provided.

4 Claims, No Drawings

(56) References Cited

OTHER PUBLICATIONS

Ornitz et al., "Receptor specificity of the fibroblast growth factor family", The Journal of Biological Chemistry 1996 271(25):15292-15297.

Arman et al., "Fgfr2 is required for limb outgrowth and lung-branching morphogenesis", Proc. Natl. Acad. Sci. USA 1999 96(21):11895-11899.

Bellusci et al., "Fibroblast growth factor 10(FGF10) and branching morphogenesis in the embryonic mouse lung", Development 1997 124:4867-4878.

Guo et al., "Keratinocyte growth factor is required for hair development but not for wound healing", Genes & Development 1996 10:165-175.

Hyatt et al., FGF-10 induces SP-C and Bmp4 and regulates proximal-distal patterning in embryonic tracheal epithelium, Am. J. Physiol. Lung Cell Mol. Physiol. 2004 287:L1116-L1126.

Min et al., "Fgf-10 is required for both limb and lung development and exhibits striking functional similarity to *Drosophila branchless*", Genes & Development 1998 12:3156-3161.

Post et al., "Keratinocyte growth factor and its receptor are involved in regulating early lung branching", Development 1996 122:3107-3115.

Sekine et al., "Fgf10 is essential for limb and lung formation", Nature Genetics 1999 21:138-141.

Lebeche et al., "Fibroblast growth factor interactions in the developing lung", Mechanisms of Development 1999 86:125-136.

Matsui et al., "FGF-2 induces surfactant protein gene expression in foetal rat lung epithelial cells through a MAPK-independent pathway", Cell Signal 1999 11(3):221-228.

Babaei et al., "Role of nitric oxide in the angiogenic response in vitro to basic fibroblast growth factor", Circ. Res. 1998 82:1007-1015.

Flamme et al., "Induction of vasculogenesis and hematopoiesis in vitro", Development 1992 116:435-439.

Hughes et al., "Therapeutic angiogenesis in chronically ischemic porcine myocardium:comparative effects of bFGF and VEGF", Ann. Thorac. Surg. 2004 77:812-818.

Ribatti et al., "Endogenous basic fibroblast growth factor is implicated in the vascularization of the chick embryo chorioallantoic membrane", Devopmental Biology 1995 170:39-49.

Ortega et al., "Neuronal defects and delayed wound healing in mice lacking fibroblast growth factor 2", Proc. Natl. Acad. Sci. USA 1998 95:5672-5677.

* cited by examiner

FETAL PULMONARY CELLS AND USES THEREOF

This patent application claims the benefit of priority from U.S. Provisional Patent Application Ser. No. 60/851,093, filed Oct. 11, 2006, teachings of which are herein incorporated by reference in their entirety This research was funded by Grant No. NIH 1R21 EB003520-01A1, and the federal government has certain rights in this invention.

INTRODUCTION

1. Field of the Invention

The present invention relates to isolated fetal pulmonary cells, engineered three-dimensional (3-D) tissue constructs of these cells, and uses thereof, for example, in identifying therapeutic agents which repair, augment and/or replace dysfunctional native lung, to perform in vitro studies, including but not limited to pharmaceutical screening, toxicity tests, developing models for lung development and disease, and characterization of mechanical injury, and to produce pulmonary tissue with a functional perfused vascular network.

2. Background of the Invention

Preterm delivery with resultant developmental lung abnormalities (i.e., pulmonary hypoplasia (PH)) is a major problem in neonatology and accounts for more than 70% of perinatal mortality (Compernolle et al. Nat Med 2002 8:702). PH is found in 15% to 20% of all neonatal autopsies, accounting for 2850 deaths yearly. The pathology of PH includes reduced lung mass, insufficient surfactant production, poorly differentiated alveolar epithelium, and a reduction of alveolar gas exchange (Leinwand et al. J Pediatr Surg 2002 37:1263).

The loss or failure of lung tissue is one of the most frequent, devastating, and costly problems in health care. The most frequently used and successful methods of therapy is transplantation. However, the severe scarcity of donor organs, especially in the pediatric population, is a major limitation and has thus stimulated investigation into selective cell transplantation and other molecular-based therapies (Pollok, J. M. and Vacanti, J. P. Semin Pediatr Surg 1996 5:191; Kim, S. S, and Vacanti, J. P. Semin Pediatr Surg 1999 8:119; Nerem, R. M. Proc Inst Mech Eng [H] 2000 214: 95; Stock, U. A. and Vacanti, J. P. Annu Rev Med 2001 52:443; Fuchs et al. Ann Thorac Surg 2001 72:577; Nerem, R. M. Ann Biomed Eng 1991 19:529).

Because of advances in tissue engineering, cell-based therapies are emerging as available treatment modalities for damaged tissues (Fuchs et al. Ann Thorac Surg 2001 72:577; and Nerem, R. M. Ann Biomed Eng 1991 19:529). Delivery of engineered cells into hypoplastic lung tissue has the potential to improve underdeveloped lung tissue and aid in restoring the process of natural tissue development. Drug delivery alone does not have the ability to achieve both of these effects.

Tissue engineering traditionally aims at the development of tissue constructs for therapeutic purposes as an alternative to organ transplantation. In addition, attempts at lung tissue engineering could potentially provide the field of lung biology with high-fidelity 3-D tissue models. The establishment of simple organotypic fetal lung cell culture models has been reported (Douglas et al. In Vitro 1976 12: 373-381; Douglas et al. Am Rev Respir Dis 1976 113:17-23; Nakamura et al. Am J Physiol Lung Cell Mol Physiol 2000 278: L974-L980; Paszek et al. Cancer Cell 2005 8: 241-254, 2005; and Schwarz et al. Am J Respir Cell Mol Biol 2004 30: 784-792). The first attempts at developing 3-D fetal lung cell culture models were reported 30 years ago by Douglas and coworkers (Douglas et al. In Vitro 1976 12: 373-381; Douglas et al. Am Rev Respir Dis 1976 113:17-23) and focused on organotypic culture of dispersed rodent fetal lung cells on 3-D substrates composed of gelatin/collagen. Additional early work focused on fetal and/or adult rodent alveolar type II (AE2) cell-enriched cultures on various matrixes, such as floating collagen membranes (Geppert et al. Exp Cell Res 1980 128: 363-374), recombined basement membrane (MATRIGEL™; Blau et al. J Cell Physiol 1988 136:203-214), and collagen gel-based systems (Sugihara et al. Am J Pathol 1993 142:783-792). Schuger et al. (Dev Biol 1996 179: 264-273) used cultures of E12-E17 murine fetal pulmonary cells (FPC) to examine how addition of soluble extracellular matrix proteins affects formation of 3-D aggregates of embryonic lung cells in agitated culture on a rotary shaker. That study focused largely on the formation of the epithelial-mesenchymal interface, but not vascular development (Paszek et al. Cancer Cell 2005 8: 241-254). Using a 3-D Gelfoam (collagen) scaffold, Nakamura et al. (Am J Physiol Lung Cell Mol Physiol 2000 278: L974-L980) utilized organotypic cultures of E19 rat FPC to determine the effects of dexamethasone and mechanical stretch on gene expression. More recently, Schwarz et al. (Am J Respir Cell Mol Biol 2004 30: 784-792) used organotypic mixtures of E15-E17 FPC seeded on two-dimensional (2-D) tissue culture plastic to investigate the role of endothelial cells (ECs) in epithelial-mesenchymal interactions. There are drawbacks, however, to 2-D culture on plastic for modeling of tissues with an epithelial component.

Previous studies have shown that primary AE2 cells cultured on 2-D plastic surfaces typically lose their phenotypic characteristics, such as surfactant protein expression and transition from a cuboidal to a flattened morphology reminiscent of type I alveolar epithelial cells (Isakson et al. Am J Physiol Cell Physiol 2001 281:C1291-C1299; Olsen et al. Exp Lung Res 2005 31:461-482; and Shannon et al. Am J Respir Cell Mol Biol 2001 24: 235-244, 2001). Some AE2 characteristics can be maintained in 2-D by plating the cells on specific extracellular matrix proteins (Isakson et al. Am J Physiol Cell Physiol 2001 281: C1291-C1299; Shannon et al. Am J Respir Cell Mol Biol 2001 24: 235-244) and supplementing the media with various hormones and growth factors (Olsen et al. Exp Lung Res 2005 31: 461-482; Shannon et al. Am J Respir Cell Mol Biol 2001 24: 235-244). In addition, 2-D coculture with lung fibroblasts enhances the differentiated properties of AE2 cells as assessed by the expression of surfactant proteins (Griffin et al. J Cell Sci 1993 105: 423-432; Linge et al. Exp Cell Res 1989 185: 519-528), stressing the importance of organotypic coculture of epithelial and mesenchymal cells. However, a major problem with cocultures of primary epithelial cells and fibroblasts, from lung and other sources, is fibroblast overgrowth.

SUMMARY OF THE INVENTION

The present invention relates to isolated murine fetal pulmonary cells, engineered 3-dimensional (3-D) organotypic pulmonary cell culture systems containing epithelial, endothelial, and mesenchymal cells, and cell-based pulmonary therapeutics for both pediatric and adult lung pathologies.

An aspect of the present invention relates to isolated murine fetal pulmonary cells comprising a mixed population of epithelial, endothelial, and mesenchymal cells.

Another aspect of the present invention relates to a technique for isolating murine fetal pulmonary cells comprising a mixed population of epithelial, endothelial, and mesenchymal cells.

Another aspect of the present invention relates to an engineered 3-D pulmonary tissue construct comprising isolated murine fetal pulmonary cells of epithelial, endothelial and mesenchymal cells and 3-D matrices permissive to cell-cell and cell-growth factor interactions.

Another aspect of the present invention relates to an engineered system for assessing effects of defined culture conditions, said system comprising an engineered 3-dimensional pulmonary tissue construct comprising isolated murine fetal pulmonary cells. This engineered system is particularly useful in performing in vitro studies, including but not limited to pharmaceutical screening, toxicity tests, models for lung development and disease and characterization of chemical or mechanical injury.

Another aspect of the present invention relates to a method for engineering pulmonary tissue with a functional, perfused vascular network comprising implanting into an animal an engineered 3-D pulmonary tissue construct comprising isolated murine fetal pulmonary cells of epithelial, endothelial and mesenchymal cells and a 3-D matrix permissive to cell-cell and cell-growth factor interactions.

Another aspect of the present invention relates to nonhuman animal models and methods for use of these nonhuman animal models to identify therapeutic agents which repair, augment and/or replace dysfunctional native lung in a human. Nonhuman animal models of the present invention are administered isolated murine fetal pulmonary cells of a mixed population of epithelial, endothelial and mesenchymal cells.

DETAILED DESCRIPTION OF THE INVENTION

The present invention provides isolated and characterized murine fetal pulmonary cells (FPC) and engineered 3-dimensional (3-D) pulmonary tissue constructs in vitro. The cells and constructs thereof provide a system which is believed to be the first 3-D organotypic cell culture model containing epithelial, endothelial, and mesenchymal cells, which describes effects of defined culture conditions on each of these cell types in an engineered system.

The system of the present invention differs significantly from existing systems, such as described by Schwarz et al. (Am J Respir Cell Mol Biol 2004 30: 784-792) in that the cells are embedded in 3-D gels, which allow for the establishment of true 3-D cell polarity. Further, the system of the present invention provides a mechanical environment more similar to that of soft tissues than rigid tissue culture plastic (Paszek et al. Cancer Cell 2005 8: 241-254).

The FPC of the present invention are preferably isolated via a technique as set forth in Example 1. This technique comprises surgically removing lungs from mouse fetuses at gestational day 18. The lungs are then minced triturated and digested to produce a cell suspension. The cell suspension is then filtered through a 70 µm filter and a cell pellet is formed from the filtered cell suspension via centrifugation. The cell pellet is then resuspended in distilled water to remove any red blood cells and washed with phosphate buffered saline containing $Ca^{2+}$ and $Mg^{2+}$. These cells are then resuspended in complete medium comprising DMEM, 10% fetal bovine serum and antibiotics.

The inventors herein first demonstrated histiotypic differentiation of FPCs of the present invention in vitro in the complex, permissive matrix MATRIGEL™, subsequently validated for other natural polymer hydrogels comprised of, but not limited to, for example collagen and/or elastin, and enhanced by addition of tissue specific growth factors. In these experiments, 3-D constructs of FPCs comprised of a mixed population of epithelial, mesenchymal and endothelial cells as assessed by immunohistochemistry and RT-PCR of 2-D cultures, were generated utilizing MATRIGEL™ hydrogel and synthetic polymer scaffolds of poly-lactic-co-glycolic acid (PLGA) and poly-L-lactic acid (PLLA) fabricated into porous foams and nanofibrous matrices, respectively. The alveolar type II (AE2) cell phenotype in 2-D and 3-D cultures was confirmed by detection of prosurfactant protein C (SpC) gene expression and presence of the SpC gene product. Three-dimensional MATRIGEL™ constructs contained alveolar forming units (AFU) comprised of cells displaying AE2 cellular ultrastructure while expressing the SpC gene and gene product. The addition of tissue specific growth factors induced formation of branching, sacculated epithelial structure reminiscent of the distal lung architecture, and endothelial cell containing capillary tube formation. Importantly, 3-D culture and the use of the mixed population of FPC was necessary for inducing expression of the morphogenesis-associated distal epithelial gene fibroblast growth factor receptor 2 (FGFr2). PLGA foams and PLLA nanofiber scaffolds facilitated ingrowth of FPC as evidenced by histology. However, these synthetic matrices did not support the survival of distal lung epithelial cells, despite the presence of tissue specific growth factors. Thus, it is believed that three dimensionality, in concert with tissue-specific cues provided by natural polymer scaffolds, and the additional of tissue-specific growth factors to the culture medium are all necessary for inducing both distal lung epithelial differentiation, vascularization and tissue morphogenesis.

The inventors also characterized differential effects of FGF10, FGF7, and FGF2 on histiotypic distal lung morphogenesis in 3-D collagen gel constructs in vitro. Numerous studies in lung developmental biology have highlighted the importance of fibroblast growth factors (FGFS) in epithelial-mesenchymal interactions that orchestrate lung development (Shannon J M and Hyatt B A Annu Rev Physiol 2004 66:625-645). FGFs play a pleiotropic role in the development of all organs, since they affect cells derived from all three embryonic germ layers. Of the 24 or so different FGFs identified as of yet, FGFs-1, -2, -7, -9, -10, and -18 are expressed in the developing lung, and so are all the fibroblast growth factor receptors (FGFRs)-1, -2, -3, and -4 (Shannon J M and Hyatt B A Annu Rev Physiol 2004 66:625-645). In the developing lung and other organs with prominent epithelial-mesenchymal FGF signaling, epithelial cells express "b isoforms" of FGFRs, whereas mesenchymal cells express "c isoforms" (White et al. Development 2006 133: 1507-1517; Zhang et al. Development 2006 133: 173-180). This distinction confers FGF ligand specificity in different cell populations (Ornitz et al. J Biol Chem 1996 271: 15292-15297). FGF10 and FGF7 are produced in the mesenchyme and signal exclusively to epithelial cells via FGFR2b (Arman et al. Proc Natl Acad Sci USA 1999 96:11895-11899; Bellusci et al. Development 1997 124:4867-4878; Guo et al. Genes Dev 1996 10: v165-v75; Hyatt et al. Am J Physiol Lung Cell Mol Physiol 2004 287: L1116-L1126; Min et al. Genes Dev 1998 12: 3156-3161; Post et al. Development 1996 22: 3107-3115; Sekine et al. Nat Genet. 1999 21: 138-141). In vitro experiments have highlighted that spatially restricted FGF10 expression in the embryonic lung mesenchyme patterns the branching/budding of the developing lung epithelium (Bellusci et al. Development 1997 124: 4867-4878; White et al. Development 2006 133: 1507-1517) and potentially plays a role in lineage specification and induction of cytodifferentiation via indirect mechanisms in vivo (Hyatt et al. Am J Physiol Lung Cell Mol Physiol 2004 287: L1116-L1126). FGF7 is expressed diffusely in the subepithelial mesenchyme and induces epithelial luminal dilation via proliferation following cessation of the FGF10-induced budding (White et al. Development 2006 133: 1507-1517). In contrast to the highly epithelial-specific FGF10, FGF2 (also known as bFGF) is more pleiotropic and binds to both the epithelial and mesenchymal isoforms of FGFRs, although higher affinity is observed for the mesenchymal c isoforms (Ornitz et al. J Biol Chem 1996 271: 15292-15297). FGF2 influences lung epithelial differentiation in vitro (Lebeche et al. Mech Dev 1999 86:125-136; Matsui et al. Cell Signal 1999 11:221-228); however, it is best known as a potent angiogenic/vasculogenic factor (Babaei et al. Circ Res 1998 82:1007-1015; Flamme I and Risau W. Development 1992 116: 435-439; Hughes et al. Ann Thorac Surg 2004 77: 812-818; Lebeche et al. Mech Dev 1999 86: 125-136; Ribatti et al. Dev Biol 1995 170:39-49). A defined role for FGF2 in lung development in vivo has yet to be established (Ortega et al. Proc Natl Acad Sci USA 1998 95: 5672-5677).

In these experiments, the morphogenic effects of the FGFs alone and in various combinations were assessed by whole mount immunohistochemistry and confocal microscopy FGF10/7 significantly increased epithelial budding and proliferation; however, only FGF10 alone induced widespread budding. FGF7 alone induced dilation of epithelial structures but not widespread budding. FGF2 alone had a similar dilation, but not budding, effect in epithelial structures, and, in addition, significantly enhanced endothelial tubular morphogenesis and network formation, as well as mesenchymal proliferation. The combination of FGF10/7/2 induced robust budding of epithelial structures and the formation of uniform endothelial networks in parallel. These data indicate that appropriate combinations of exogenous FGFs chosen to target specific FGF receptor isoforms allows for control of lung epithelial and mesenchymal cell behavior in the context of an engineered system. Further, these experiments demonstrate use of an engineered system of the present invention as an in vitro model of fetal distal lung tissue for investigating, for example, lung developmental biology, in particular dynamic epithelial-endothelial interactions, and to dissect the role of mesenchymal cells in these processes.

As shown herein, in natural polymer scaffolds such as MATRIGEL™, the collagen type I gel system or elastin, differential morphogenetic responses of epithelial and endothelial cells is observed in a mixed culture of murine fetal pulmonary cells depending on the growth factor composition of a serum-free defined medium. Thus, it is believed that the tissue-engineered fetal distal lung constructs of the present invention provide a potential source of tissue or cells for lung augmentation in pediatric pulmonary pathologies, such as pulmonary hypoplasia and bronchopulmonary dysplasia. In addition, engineered systems provide alternative in vitro venues for the study of lung developmental biology and pathobiology and for drug screening and toxicity testing.

In 3-D constructs of the present invention, concerted epithelial and endothelial morphogenesis is impacted by organotypic coculture and addition of exogenous FGFs. As shown herein, however, coculture and serum-free culture with FGF10/7/2 alone is insufficient to induce epithelial morphogenesis or maintain SP-C gene expression in extended cultures on synthetic polymer scaffolds. Further, in 3-D collagen gel constructs, endogenous signaling elaborated in serum-free culture in the absence of exogenous FGFs was insufficient to induce epithelial or endothelial morphogenesis. An increase in the number of dead cells in cultures maintained with 1% ITS only suggests that, in the absence of serum, exogenous FGF10/7/2 function in part as survival/mitogenic factors for FPC cultured in collagen gels. The experiments performed indicate that FGF10/7 alone induce an approximately four-fold increase in epithelial cell numbers in AFUs, whereas FGF2 alone induces a similar approximately four-fold increase in mesenchymal cell numbers, which is combined additively in FGF10/7/2 cultures. Taken together, these experiments indicate that FGF10/7/2 enhance viability and proliferation of FPC in 3-D culture, whereas the mechano-spatial cues present in compliant hydrogels, such as MATRIGEL™ and collagen gels, appear to allow for a morphogenic response. By contrast, the response of these cells to rigid polymer scaffolds is similar to 2-D culture.

Accordingly, for engineered systems of the present invention, a 3-D matrix permissive to cell-cell and cell-growth factor interactions such as, but not limited to, a hydrogel based natural collagen or elastin scaffold or MATRIGEL™ scaffold, is preferred. It is expected that scaffolds, more preferably a hydrogel based scaffold comprising a mixture of natural polymers and synthetic polymers permissive to cell-cell and cell-growth factor interactions can also be used. To produce an organotypic fetal lung tissue construct in accordance with the present invention, the 3-D matrix permissive to cell-cell and cell-growth factor interactions is seeded with FPC cells of the present invention and is cultured with tissue specific growth factors. In a preferred embodiment, the 3-D matrix permissive to cell-cell and cell-growth factor interactions is seeded with FPC cells of the present invention and is cultured in a serum-free medium containing FGF10, FGF7 and/or FGF2.

An engineered tissue construct of the present invention was also demonstrated to provide an in vivo angiogenesis model used to establish a correlation between host inflammatory response and angiogenesis. For this model, FPC of the present invention were mixed with liquid MATRIGEL™ in the absence and presence of polyvinyl sponges loaded with 100 ng bFGF and injected subcutaneously into C57BL/6 mice. Prior to harvesting the MATRIGEL™ plugs after 7 days, functional vascularization was first ascertained by tail vein injection with FITC-dextran followed by fluorescent microscopic visualization of the excised plugs. Histological sections of the plugs were stained with H&E and antibodies against cytokeratin and surfactant protein C for epithelial cells. CD3 was utilized as a marker for invading T-lymphocytes. All harvest plugs contained AFUs and patent blood vessels. Addition of bFGF significantly enhanced neovascularization in all cases. Plugs containing allogeneic FPC demonstrated only marginally increased vascularization, despite an approximate 2-fold increase in inflammatory response, as evidenced by quantification of FITC-dextran vessel perfusion and CD3 staining, respectively. Importantly, perfused neovessels within the constructs contained both host and graft derived endothelial cells. Thus, taken together, these results indicate that exogenous angiogenic factors, in this case bFGF, are more potent stimulators of angiogenesis than inflammatory cytokines in this system. These results also demonstrate the usefulness of this implanted system as a natural bioreactor for engineering pulmonary tissue with a functional, perfused vascular network.

As will be understood by the skilled artisan upon reading this disclosure, these natural bioreactors can be prepared from other natural polymer scaffolds including, but not limited to collagen or elastin gel systems as well as scaffolds comprising a mixture of natural polymers and synthetic polymers permissive to cell-cell and cell-growth factor interactions.

Further, the engineered pulmonary tissue constructs of the present invention may comprise additional cell types to the FPC seeded simultaneously with the FPC or added at a later time. For example, in one embodiment, the engineered tissue construct may comprise mast cells in addition to FPC. Inclusion of mast cells in the engineered tissue construct provides for examination of inflammatory processes in pulmonary tissue such as those occurring in asthma.

The engineered pulmonary tissue constructs of the present invention provide a useful means for identifying therapeutic agents which repair, augment and/or replace dysfunctional native lung, performing in vitro studies, including but not limited to pharmaceutical screening and toxicity tests, and developing models for lung development and disease, and characterization of mechanical injury. For example, in one embodiment, the pulmonary tissue construct is used to assess pharmaceutical activity and/or toxicity of an agent in pulmonary tissue. In this method, the engineered 3-dimensional pulmonary tissue construct is contacted with the agent and an effect of the agent on the engineered 3-dimensional pulmonary tissue construct is measured. Exemplary effects which can be measured include, but are in no way limited to, cell death and alterations in histiotypic differentiation of the fetal pulmonary cells to epithelial and vascular components with branching morphology and arranged as alveolar forming units.

The present invention also relates to nonhuman animal models and methods for their use in identifying therapies to repair, augment and/or replace dysfunctional native lung in a subject and/or to study lung development and disease and/or to characterize mechanical injury of pulmonary tissue.

Reliable and reproducible methods for delivering FPCs to a live animal model of PH were developed. In these experiments, three methods of delivery were explored: intraoral, intratracheal, and intrapulmonary injection. Adult Swiss Webster mice were anesthetized and fluorescent labeled microspheres (20 μm diameter) were delivered by intraoral and intratracheal injection. Subsequently, labeled FPC (Cell Tracker, CMTPX; Molecular Probes, Eugene, Oreg.) were delivered by the same methods. In addition, direct transpleural, intrapulmonary injection of FPC was performed. Outcome analysis included survival, reproducibility, diffuse versus confined location of the injected substance, and adequacy of delivery. Routine histological examination, fluorescent microscopy, and immunostaining were performed.

Delivery of substances into the pulmonary parenchyma via the intraoral route was first examined using cell-sized fluorescent microspheres as cell surrogates. The quality of the injection was defined as "adequate delivery" if more than 10 microspheres were identified per 400× high power field. These results were assessed in randomly acquired images from harvested lungs of eight mice. Three of the injections were identified as adequate (37.5%) and five as poor (62.5%).

The intratracheal route, which ensures direct placement of the needle into the trachea, was also examined initially with microspheres being administered intratracheally to 23 mice. Two animals were excluded from the analysis due to intraoperative death. One animal died due to excessive dissection and pneumothorax and the second due to buprenorphine overdose. Of the 21 mice included, 16 were identified as adequate injections (76.2%) and five as poor (23.8%) (P<0.05).

Animals were then administered labeled FPCs intratracheally, intraorally or via intrapulmonary delivery and H & E and fluorescent micrographs of serial lung sections after intratracheal, intraoral, and intrapulmonary delivery of labeled FPC were examined to assess the percentage of animals with adequate delivery in the intratracheal and intraoral groups.

Of a total of 11 mice administered labeled FPC intraorally, six were identified as adequate (54.5%) and five as poor (45.5%). Comparing the microsphere delivery intraorally with the labeled FPC delivery intraorally, there was a trend for an improvement in the number of adequate injections from 37.5% to 54.5% (P=NS).

A total of 23 mice were administered labeled FPC by intratracheal injection. One animal was excluded due to excessive dissection leading to pneumothorax and immediate intraoperative death. Of the 22 mice included, 10 were identified as adequate injections (45.5%), and 12 as poor injections (54.5%). Given the high rate of poor injections (54.5%), further intratracheal experiments with microspheres were carried out to improve the technique and limit amount of animal usage. To allow for comparison and standardization of tissue autofluorescence, an intratracheal experiment with unlabeled FPC was included.

The intratracheally delivered labeled FPC showed evidence of transepithelial migration after 7 days of in vivo culture. Fluorescent micrographs in which labeled FPC are seen showed labeled FPCs in the alveolar lumen as well as the lung parenchyma. In addition, co-localization of Type 2 alveolar epithelial cells with prosurfactant protein C and labeled FPC was observed, which indicating that alveolar Type 2 cells of donor origin may integrate into the lung epithelium/parenchyma.

Labeled FPC were also administered via intrapulmonary administration to 16 mice. Experiments with microspheres were not carried out in this experimental subset since the intrapulmonary route delivers the substance directly into the lung parenchyma. The mortality rate associated with this procedure was 6.25%. Intrapulmonary injection of labeled FPC resulted in the formation of pockets of cells that did not appear to disperse throughout the tissue. These cells did not form any discernable structures within the pockets. In addition, the pockets formed by intrapulmonary injection did not interface with the surrounding tissue and incited an apparent local fibrotic response. In these intrapulmonary injections, no hemorrhage on H and E staining occurred in the host lungs. However, due to the inability to visualize the path of the needle, 6.25% of intrapulmonary injections resulted in severe hemorrhage and lung injury.

Thus, as demonstrated by these experiments, delivery of cells into live animals via all three routes is feasible. Preferred as most reliable and having a reproducible route for diffuse delivery of cells into the distal airways is intratracheal administration.

Further, administration of labeled FPC into the distal airways via direct intratracheal (tracheotomy) or intraoral injection resulted in a relatively uniform distribution of engrafted FPC in the peripheral airway tissue in adequate injections. This indicates that administration of cells via the airways is a viable method of distributing cells widely within the lung parenchyma. In addition, intratracheal delivery of labeled FPC resulted in transepithelial migration of cells 7 days after injection. This finding is significant since it indicates that it is possible for cells delivered intratracheally to intercalate into the distal airways and enter the lung parenchyma. This phenomenon is a requirement for cell-based therapy of lung disorders such as PH to be successful.

In addition, phenotypic characterization of the labeled FPC indicated that a subpopulation of the injected FPC maintained Type 2 alveolar cell phenotype. This indicates that administration of FPCs of the present invention, preferably via the intratracheal method, to, for example, a diseased animal model provides a means for translational research useful in identifying therapeutic agents, including but in no way limited to cell-based pulmonary therapeutics, to augment and/or replace dysfunctional native lung in humans.

The following nonlimiting examples are provided to further illustrate the present invention.

EXAMPLES

Example 1

Fetal Pulmonary Cell Isolation and In Vitro Culture

Embryonic day 17.5 (E17.5) murine FPC were obtained from the lungs of timed-pregnant Swiss Webster mouse fetuses at gestational day 18 (Charles River Laboratories, Wilmington, Va.). Specifically, fetal lungs were surgically removed, rinsed in Hanks Balanced Salt Solution (HBSS; Cellgro, Herndon, Va.), minced, triturated and digested with 0.5% trypsin in PBS for 5 and 20 minutes, respectively. Following quenching of the trypsin with Dulbecco's modified Eagle medium containing FBS (Cambrex, East Rutherford, N.J.) and filtration through a 70 µm filter (BD Falcon, San Jose, Calif.), the cell suspension was pelleted for 5 minutes at 800 rpm. The pellet was resuspended for 30 seconds in 900 µL distilled water to remove the RBCs by hypotonic lysis, followed by the addition of 100 µL of 10×PBS (Cellgro). The cells were washed once more in 1×$Ca^{2+}$/$Mg^{2+}$ containing PBS, and resuspended in complete medium (DMEM+10% fetal bovine serum+antibiotics).

Cell viability was assessed in a fluorescent microscope using the live/dead assay (Molecular Probes, Eugene, Oreg.), according to the manufacturer's instructions. For the initial 24 hours, primary isolates were cultured in DMEM medium (Cambrex), supplemented with 10% fetal bovine serum (Hyclone, Logan, Utah), L-glutamine, penicillin-streptomycin antibiotics, and 1% insulin-transferrin-selenium (ITS) supplement containing linoleic acid and BSA (BD Biosciences, San Jose, Calif.). After 24 hours, the culture media was switched to one of two serum containing media formulations; namely either serum-free DMEM with the same supplements as discussed supra (SF-ITS) or a serum-free, tissue-specific, growth factor-defined medium (SF-GF) containing FGF-7 (12.5 ng/ml), FGF-10 (25 ng/ml), and bFGF (12 ng/ml) in an 8:2 mixture of DMEM:F12 with L-glutamine and penicillin-streptomycin antibiotics was used to enhance epithelial cytodifferentiation and tissue construct morphogenesis.

For cells in a collagen matrix, following initial isolation, the FPC were centrifuged and resuspended in a 1.2 mg/ml liquid collagen solution (BD Biosciences) at physiological pH, at a density of 2.5-5.0 million FPC/ml. One milliliter of cell/collagen mixture per well was cast in 24-well plates and transferred to the incubator. Following polymerization of the gel, 2 ml of an 80:20 mixture of DMEM-F-12 medium (Cambrex) containing 10% FBS (Hyclone), L-glutamine, and penicillin-streptomycin antibiotics were overlaid, and the constructs were incubated overnight. Subsequently, the constructs were maintained in 2 ml serum-free basal DMEM/F-12 medium supplemented with 1% insulin-transferrin-selenium (1% ITS; BD Biosciences) and heparin (10 U/ml; Sigma); 10% FBS; or 1% ITS supplemented with FGF7 (10 ng/ml), FGF10 (25 ng/ml) or FGF2 (25 ng/ml) alone or in combination as follows: FGF10, FGF7, FGF2, FGF10/7, FGF10/7/2. All cell culture was carried out at 37° C. in a 5% $CO_2$ humidified incubator. The medium was replaced every 48 hours for the 1st week, then every 24 hours for cultures that were extended to 14 days.

Example 2

Immunohistochemistry of FPCs

Identification of AE2 cells and epithelial cells in cultures of the present invention was carried out by indirect immunohistochemistry in accordance with procedures described by Yuli and Lelkes (Eur. J. Biochem. 1991 177:1). Specifically, fetal pulmonary cells were cultures in tissue culture chamber slides (Fisher) coated with MATRIGEL™ (BD Biosciences), type I collagen (BD Biosciences), and poly-D_lysine (Sigma, St. Louis, Mo.) matrices. At various time points (1-4 days post plating), the cultures were fixed with 10% neutral buffered formalin (Formalde-Fresh, Fisher) for 15 minutes at room temperature, washed with Tris buffered saline (TBS, pH 7.4) and permeabilized with 25 µM digitonin (in TBS) for 10 minutes. For visualization with peroxidase-labeled secondary antibodies, the samples were treated for 5 minutes with 3% $H_2O_2$ in methanol to block endogenous peroxidase activity. For paraffin-embedded samples, sections were deparaffinized and rehydrated according to standard protocol, washed with TBS containing 1% BSA, and exposed to the same peroxidase blocking steps. All subsequent washing and incubation procedures were carried out in TBS containing 1% BSA to block nonspecific staining. In the case of paraffin-embedded samples, an additional blocking step with 3% BSA in TBS pH 7.4 for 30 minutes was implemented. In the case of vimentin immunostaining, the use of a monoclonal mouse antibody necessitated the use of a Mouse2Mouse kit (Syctek, Logan Utah) containing specific blocking agents for mouse tissue and cells. The slides were incubated for 45-90 minutes at room temperature with polyclonal rabbit primary antibodies against prosurfactant protein C (1:500, Chemicon, Temecula, Calif.), cytokeratin (1:500, Dako, Carpinteria, Calif.), and vimentin (1:100, Santa Cruz Biotechnology, Santa Cruz, Calif.). Negative controls were processed by omission of the primary antibody and/or utilizing preimmune serum of the animal where the primary antibody was raised. After rinsing each with TBS three times for 1 minute, the slides were incubated for 30 minutes with either fluorescent (1:1000, Alexa 488 conjugated, goat anti-rabbit IgG for cytokeratin staining; Molecular Probes) or immunoperoxidase conjugated secondary antibody (Dako AEC+kit, prosurfactant C and cytokeratin staining or Syctek M2M kit, vimentin). If desired, samples stained with fluorescent DNA stain bisbenzimide (2 µg/ml; Hoechst 33258, Sigma) and/or rhodamine-phalloidin (1 µg/ml; Sigma) and viewed on a fluorescent microscope (Leica DMRX, Wetzlar, Germany). Peroxidase-stained samples were counterstained for 30 seconds with hematoxylin (Fisher). Endothelial cells were stained with a murine endothelial specific marker GSL I isolectin $B_4$ (GSL Iso $B_4$) (FITC-conjugate from the African legume, *Griffonia simplicifolia*; Vector Labs, Burlingame, Calif.). Specifically, cells were fixed in formalin and incubated in a 5 µg/ml FITC-conjugated GSL Iso B4 lectin solution, containing bisbenzimide and rhodamine-phallodoin for counterstaining, prepared in 1×PBS for 10 minutes, washed three times for 1 minute in 1×PBS, and viewed with a Leica fluorescent microscope. Percentages for individual cell counts were obtained by means of automated counting of GSL Iso B4 and cytokeratin-positive cells in 45 individual fields across three independent experiments (15 fields per experiment).

Example 3

Reverse Transcriptase Polymerase Chain Reaction

Reverse transcriptase polymerase chain reaction (RT-PCR) was utilized to detect steady-state mRNA expression of relevant genes; surfactant protein C (SpC) for AE2 cells and vimentin for cells of mesenchymal origin. For RT-PCR, total RNA was isolated from 2-D cultures growing on MATRIGEL™ collagen, and poly-D-lysine substrates using the RNeasy column method (Quiagen, Valencia, Calif.) with an additional DNA digestion step to remove contaminating genomic DNA. Total RNA was isolated from 3-D MATRIGEL™ hydrogels and synthetic polymer scaffolds by digestion with TriReagent (Sigma) and subsequent purification of the RNA-containing aqueous extraction phase on an RNeasy column (Quiagen), according to the manufacturer's protocols. The quality of isolated RNA was assessed by measuring the ratio of $OD_{260}/OD_{280}$ and by electrophoresis in 1% agarose formamide gels with ethidium bromide containing loading buffer. The isolated RNA was reverse transcribed using a commercial RT kit (Promega, Madison, Wis.), according to the manufacturer's instructions; the resultant complimentary DNA was used for PCR amplification. Specifically, the cDNA was added to a reaction mixture containing 1.5 mM magnesium chloride, 10 mM dNTP, 2% v/v Taq enzyme, and 15 µM forward and reverse primers optimized for each gene of interest in preliminary experiments. For all genes, a 35 cycle 2-step PCR routine with a 45 second denaturation step at 94° C. and an 80 second combined annealing and extension step at 68° C. was used. Negative controls run for all PCR reactions included no reverse transcription samples to check for genomic DNA, as well as reactions without the additional of the cDNA templates. The primer sequences used in characterization of FPC populations are shown in Table 1 (Clontech Atlas Mouse 1.2 Array II, Cat. #7857-1, BD Biosciences).

Example 5

Poly L-lactic-co-glycolic acid Sponges

Porous sponges, composed of 90% polylactic acid-10% polyglycolic acid (90:10 PLGA) were used for 3-D culture of fetal pulmonary cells (Key National Polymer Laboratories, Changchun, China). The scaffolds were fabricated using NaCl as a poragen. The scaffolds were trimmed to approximately 5×5 mm cubes and sterilized with 70% ethanol prior to use.

Example 6

Scaffold Seeding

MATRIGEL™ hydrogels were created by admixing either 100,000 FPC/ml or 1,000,000 FPC/ml into liquid MATRIGEL™ at a 1:9 volume ratio (cell suspension-MATRIGEL™) under aseptic conditions and inducing gelation by incubation at 37° C. Prior to seeding, PLGA porous foams and PLLA nanofiber matrices were sterilized by soaking in 70% ethanol for 1 hour, followed by air drying and prewetting in serum-free DMEM. Murine fetal pulmonary cells were seeded onto the electrospun PLLA nanofiber matrix and the PLGA porous sponges by dynamic seeding of scaffolds with high-density cell suspension overnight in an orbital shaker (Belly Dancer, Stovall, Greensboro, N.C.). A cell suspension of 500,000-1,000,000 cell/ml was found to be optimal. The total time period for dynamic seeding was approximately 24

TABLE 1 cDNA Primer Sequences Used for Reverse Transcriptase Polymerase Chain Reaction

| Gene | Forward Primer | Reverse Primer | Product Length |
|---|---|---|---|
| SpC | AGCGAGCAGACACCATCGCTACC (SEQ ID NO:1) | CTCGGAACCAGTATCATGCCCTTC (SEQ ID NO:2) | 242 |
| Vimentin | GCTCGCTCGGCGGCTAGGATG (SEQ ID NO:3) | CTGGTAGACATGGCTTCGAAGGTG (SEQ ID NO:4) | 218 |
| FGF10 | AGATAACATCAGTGGAAATCGGAGTTG (SEQ ID NO:5) | GTACATTTGCCTGCCATTGTGCTGC (SEQ ID NO:6) | 197 |
| FGFr2 | GAGAGCACCGTACTGGACCAACAC (SEQ ID NO:7) | GACCACACTTTCCATAATAAGGCTCC (SEQ ID NO:8) | 214 |

Example 4

Fabrication of PLLA Nanofiber Scaffolds by Electrospinning

An electrospinning solution was prepared by adding 1.25 grams poly-L-lactic acid to 40.625 grams of chloroform (Sigma) while stirring and heating the solution to 50° C. After 1 hour, 8.125 grams of dimethyl formamide (Sigma) was added under continued stirring. The final concentration of PLLA used for electrospinning was 2.5 wt. %. The PLLA solution was loaded into a calibrated syringe pump (KD Scientific Single-Syringe Infusion Pump, Fisher, 14-831-1). Electrospinning was carried out using the following system parameters; electrical field strength of 25 kV (1.25 kV/cm spin distance of approximately 12 cm, with a spinning time of approximately 6 hours. The effective thickness of PLLA nanofibers was 1-2 mm.

hours. Following dynamic seeding, scaffolds were cultured for up to 4 weeks in static conditions and for select experiments in 55 ml rotating wall vessel reactors (RWV, Synthecon, Houston, Tex.) for up to 14 days. All RWV experiments were carried out with SF-ITS medium. All experiments investigating the effect of growth factors on culture in 3-D polymer scaffolds were carried out under static conditions in 12-well plates.

Example 7

Histology

All 3-D assemblies were processed for histology (H&E staining). Specifically, formalin fixed samples were dehydrated through a series of graded alcohols, cleared with xylene, and embedded with paraffin was according to standard protocol as described by Kanda et al. (Endothelium 1998

6:33), Silverman et al. (Am. J. Physiol. 1999 277:C233) and Papadimitriou et al. Endometrium 1993 1:207). Ten micrometer sections were cut using a rotary microtome (Leitz 1512), de-paraffinized, rehydrated and stained with H&E.

Example 8

Transmission Electron Microscopy

The ultrastructure of 3-D cultures maintained in vitro for 4 weeks in MATRIGEL™ gel and electrospun fibrous scaffolds, respectively, were examined in accordance with procedures described by Lazarovici et al. (FEBS Lett 1989 253: 121). Samples were washed with cold 0.2 M Na cacodylate buffer (pH 7.4) and fixed overnight with 2.5% glutaraldehyde in cacodylate buffer. Following an additional wash in buffer, the samples were post-fixed with 2% $OsO_4$ in cacodylate buffer (1 hour, 4° C.), dehydrated in graded concentrations of cold ethyl alcohol, and embedded in epoxy resin. Ultrathin sections were examined with a Zeiss EM 109 microscope operated at 80 kV. At the time of sectioning for TEM, semi-thick sections were prepared for toluidine staining to examine the overall cellular morphology within the constructs.

Example 9

Whole Mount Immunohistochemistry

Morphologic and phenotypic characterization of in vitro constructs was carried out using a whole mount indirect fluorescent immunohistochemistry protocol similar to that used for whole mount staining of embryos and explants as described by Sillitoe RV and Hawkes R (J Histochem Cytochem 2002 50: 235-244) and Snow et al. (Anat Rec A Discov Mol Cell Evol Biol 2005 282: 95-105). Specifically, 3-D constructs were fixed in 4% paraformaldehyde (Electron Microscopic Sciences) for 1 hour at room temperature and then overnight at 4° C. and washed 3×20 minutes in 1×TBS containing 100 mM glycine (Sigma), pH=7.4, to reduce background autofluorescence. All steps were performed at room temperature on a bench-top orbital shaker (Belly Dancer; Stovall). Constructs were washed briefly in 1×TBS and then permeabilized/blocked using 0.5% Triton X and 3% BSA in 1×TBS for 6-8 hours. Following the permeabilization and blocking, constructs were washed 3×5 minutes in 1×TBS with 1% BSA. Constructs were then incubated with either polyclonal rabbit primary antibodies against pan-cytokeratin to visualize the intermediate filaments in all epithelial cells (1:100; Dako), prosurfactant protein C (pro-SP-C) to identify type II alveolar epithelial cells (AE2, 1:100; Chemicon), platelet endothelial cell adhesion molecule (PECAM)-1 (1:50; Abcam) to identify endothelial cells (ECs), and tropoelastin (1:100; Abcam) as a marker for mesenchymal cells. All primary antibodies were prepared in 1×TBS containing 0.1% Triton X and 1% BSA. Negative controls were processed identically, except that the specific primary antibodies were replaced with normal rabbit IgG (1:50 to 1:100). After washing 3×1 minutes with 1×TBS, the constructs were washed 3×20 min in 1×TBS with 1% BSA and then for 2 hours in a large volume (15-ml tube for each sample) of 1×TBS. Samples were then washed once more with 1×TBS+ 3% BSA+0.2% Triton X for 30 minutes before secondary antibody application. Secondary antibodies, fluorescent goat anti-rabbit IgGs (Alexa488 or Alexa594; Invitrogen), were prepared at dilutions of 1:500 in 1×TBS containing 0.1% Triton X and 1% BSA and incubated with constructs for 2 hours. Endothelial cells were identified by staining with *Griffonia simplicifolia* lectin I-isolectinB4 (isoB4; Invitrogen). Depending on the multistaining protocol, isoB4 was used conjugated to either Alexa488, Alexa568, or Alexa647. The endothelial specificity of isoB4 reported previously by Akeson et al. (Pediatr Res 2005 57: 82-88), Hyink et al. Am J Physiol Renal Fluid Electrolyte Physiol 1996 270: F886-F899) and Laitinen L. (Histochem J 1987 19: 225-234) was. For multiplex immunocytochemistry of vascular endothelial cell growth factor receptors (VEGFRs) and FGFRs, commercially available kits (Zenon anti-rabbit Alexa dye labeling kits) were used to generate fluorescent conjugates of rabbit polyclonal antibodies against VEGFR1 and VEGFR2 (Neomarkers) and FGFR1 and FGFR2 (Abgent) according to the manufacturer's instructions. Primary fluorescent antibody conjugates were used at 1:50 dilutions for 30 minutes. Staining patterns were confirmed by comparison with single-target indirect immunofluorescence in separate experiments. When double staining with isoB4 was performed, a 10 μg/ml solution of the desired isoB4 conjugate was prepared and admixed to either the secondary antibody solution or along with the primary conjugates used for multiplex immunocytochemistry. Finally, all constructs were washed 3×20 minutes with 1×TBS, then for 2 hours in a large volume of 1×TBS (15-ml tube for each sample) before being mounted with antifade medium (Vectashield; Vector Laboratories), and visualization by laser-scanning confocal microscopy (Leica). Digital images were acquired using proprietary software from Leica for conventional and confocal microscopy. 3-D z-projections of whole mount staining were generated using the Leica confocal software.

Example 10

Quantitative Image Analysis and Statistical Analysis

Quantitative analysis of phase-contrast images of alveolar-forming units (AFUs) taken at 7 days for epithelial morphometry was carried out using NIH Image J. Images were all taken at ×100 magnification. For each sample/condition/experiment, a minimum of 10 images containing approximately 25 individual AFUs were analyzed. Individual AFUs were manually outlined using the region of interest selection tool. Once selected, the area of individual AFUs (pixels) was measured. Normalized areas were calculated for each independent experiment, setting 1% ITS equal to 1. Normalized mean areas for each independent experiment were then averaged to yield a cumulative value. The data are represented as degree of increase over 1% ITS. Rudimentary bud counts for individual AFUs were performed manually in parallel with area measurements, and the results were normalized to 1% ITS in a similar fashion. Statistical analysis of the area measurements and bud counts was carried out by one-way ANOVA with the Tukey posttest (t-test) for individual comparisons between area values for the various media supplementation conditions.

Quantification of isoB4 staining in laser-scanning confocal micrographs was also carried out using NIH Image J. For each experimental condition, at least 20 randomly acquired ×200 fields were analyzed at comparable z-positions taken from at least two whole mount constructs. Individual images were binarized, and total area of isoB4-stained pixels per ×200 microscopic field was calculated. With the same data, a morphogenetic index, termed the index of elongation and interconnectivity, was determined by measuring the fraction of total area of isoB4 staining contributed by interconnected/elongated EC area vs. single EC area [index=area of interconnected EC/(area of interconnected EC+area of single EC)].

These values are basically zero for 1% ITS and 10% FBS cultures. Statistical analysis of the area measurements was carried out by one-way ANOVA with Tukey's posttest (t-test) for individual comparisons between area values for the various media supplementation conditions. P values were calculated by Student's t-test with P<0.05 being regarded as statistically significant.

Example 11

Viability Staining

Cell viability was assessed at 7 days in select experiments by using the LiveDead kit (Invitrogen). Specifically, following removal of cell culture medium, 1 ml of 2 μM ethidium homodimer and 4 μM calcein-AM in 1×PBS were added to the constructs, which were then incubated for 30-45 minutes at room temperature on an orbital shaker. Samples were then washed with 1×PBS (3×5 minutes) and immediately imaged on a fluorescent microscope (Leica). Imaging was delicate, since the unfixed samples were fragile. Photobleaching of the calcein-AM during focusing in the 3-D gels was also problematic. Nevertheless, differences in the viability of cells in constructs cultured with the various media were clearly discernible.

Example 12

Methods of In vivo Injection

Intraoral Injection

Adult Swiss Webster mice were anesthetized with isofluorane. Direct laryngoscopy with a small spatula was performed and a 24 gauge angiocathether was inserted into the oropharynx to deliver either microspheres (100 μL suspension, microsphere solution diluted 1:1 in 10× phosphate-buffered saline [PBS] or fluorescently labeled fetal pulmonary cells (10 million CMTPX CellTracker labeled FPC suspended in 100 μL of medium as described below).
Intratracheal Injection Adult Swiss Webster mice were anesthetized with isofluorane. A small incision was made over the anterior neck in a transverse fashion. Blunt dissection was used to identify the trachea and a 27 gauge needle was inserted between the tracheal rings. Microspheres or labeled FPC (10 million labeled FPC suspended in 100 μL of medium) were delivered as described below. Adequate injection was evidenced by visualization of the suspension through the tracheal tissue with minimal reflux of suspension back through the nose. Pain relief was obtained with buprenorphine (0.2 mL Buprenex diluted 1:100 in 10×PBS) injected subcutaneously before termination of the procedure. The incision site was closed with 4-0 silk sutures.
Intrapulmonary Injection Adult Swiss Webster mice were anesthetized with isofluorane and a skin incision was made over the right chest. The muscle layers were dissected sharply until the lung was visualized through the intercostal spaces. With a 27 gauge needle 10 million labeled FPC in 100 μL of 1 mg/mL collagen Type 1 solution (BD Biosciences, San Jose, Calif.) were injected through the intercostal space directly into the lung parenchyma. The collagen solution was used as a delivery vehicle to localize the distribution of the engrafted cells, as the collagen solution gels rapidly at 37° C. The skin was closed in an interrupted fashion with 4-0 silk sutures. Buprenorphine was administered subcutaneously for pain relief as described above.

Example 13

Spheres and Labeled FPC

Sphere Delivery

One hundred μL of a solution containing fluorescent microspheres (microspheres diluted 1:1 in 10× phosphate buffered saline (PBS), yellow; 20 μm diameter, Polysciences, Warrington, Pa.) were administered with a 24 gauge angiocatheter intraorally or with a 27 gauge needle intratracheally. After the procedure, the animals were housed overnight. Lungs were harvested on the next day, washed in 10×PBS and fixed in paraformaldehyde overnight. Tissue was embedded in OCT compound (Triangle Biomedical Sciences, Durham, N.C.), snap-frozen at −80° C. and stored at −80° C. Thirty micron sections were prepared with a cryostat. Slides were mounted with Vectashield mounting medium containing DAPI (Vector Laboratories, Burlington, Calif.) for nuclear counterstaining.
Cellular Delivery Labeled FPC were administered intraorally, intratracheally or intrapulmonary, as described in the preceding example.

Example 14

Labeling FPCs

To identify the injected FPC in vivo, the cells were labeled in vitro with Cell Tracker (CMTPX; Molecular Probes, Eugene, Oreg.), a fluorescent probe that is retained in living cells through several generations. It is not transferred to adjacent cells. The labeling procedure, performed according to the manufacturer's instructions, consisted of incubating the cells with 25 μm CMTPX for 30 minutes in serum-free medium, followed by three 5 minute washing steps in 1×PBS. The CMTPX CellTracker passes freely through cell membranes and, unlike some of the other CellTracker dyes, it does not require enzymatic activity once in the cell to activate fluorescence.

Example 15

Housing, Harvesting and Sample Processing

After the surgical procedure, the animals were housed for up to 1 week, depending on the protocol when the lungs were harvested. Following harvesting, the lungs were washed in 10×PBS and fixed in paraformaldehyde overnight. Routine histology and immunostaining for surfactant protein C (ProSpC, Type 2 alveolar epithelial cells) were performed. Identification of alveolar epithelial cells was carried out by immunofluorescence as previously described by Yuli and Lelkes (Eur J Biochem 1991 201:421).

Example 16

Statistical Analysis

Comparison of intraoral (IO) versus intratracheal (IT) injection was performed in both the microsphere group and the labeled FPC group. Examination of serial micrographs was performed and the percentage of animals with adequate delivery was calculated as the adequate delivery/inadequate delivery×100. The adequate delivery percentage was then compared between groups (IO versus IT) and analyzed statistically using Fisher's exact test, with P<0.05 considered statistically significant. Error bars represent variance.

What is claimed is:

1. An engineered three-dimensional pulmonary tissue construct comprising: 1) a mixed population of fetal pulmonary cells, wherein said population comprises epithelial, endothelial, and mesenchymal cells, wherein said cells exhibit enhanced viability and proliferation, 2) a three-dimensional matrix of natural polymer hydrogels comprising collagen or elastin, wherein said matrix is permissive to cell-cell and cell-growth factor interactions, and 3) a combination of fibroblast growth factors (FGF) comprising FGF10, FGF7, and FGF2, wherein the combination of FGF10/7/2 induces robust budding of epithelial structures and the formation of uniform endothelial networks in parallel.

2. The engineered three-dimensional pulmonary tissue construct of claim 1, wherein the three-dimensional matrix comprises MATRIGEL™ or a mixture of a synthetic polymer and collagen or elastin.

3. The engineered three-dimensional pulmonary tissue construct of claim 1 further comprising mast cells.

4. A method for engineering pulmonary tissue with a functional, perfused vascular network comprising implanting into an animal the engineered three-dimensional pulmonary tissue construct of claim 1.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: Artificial sequence
<220> FEATURE:
<223> OTHER INFORMATION: Synthetic

<400> SEQUENCE: 1
agcgagcaga caccatcgct acc                                         23

<210> SEQ ID NO 2
<211> LENGTH: 24
<212> TYPE: DNA
<213> ORGANISM: Artificial sequence
<220> FEATURE:
<223> OTHER INFORMATION: Synthetic

<400> SEQUENCE: 2
ctcggaacca gtatcatgcc cttc                                        24

<210> SEQ ID NO 3
<211> LENGTH: 21
<212> TYPE: DNA
<213> ORGANISM: Artificial sequence
<220> FEATURE:
<223> OTHER INFORMATION: Synthetic

<400> SEQUENCE: 3
gctcgctcgg cggctaggat g                                           21

<210> SEQ ID NO 4
<211> LENGTH: 24
<212> TYPE: DNA
<213> ORGANISM: Artificial sequence
<220> FEATURE:
<223> OTHER INFORMATION: Synthetic

<400> SEQUENCE: 4
ctggtagaca tggcttcgaa ggtg                                        24

<210> SEQ ID NO 5
<211> LENGTH: 27
<212> TYPE: DNA
<213> ORGANISM: Artificial sequence
<220> FEATURE:
<223> OTHER INFORMATION: Synthetic

<400> SEQUENCE: 5
agataacatc agtggaaatc ggagttg                                     27

<210> SEQ ID NO 6
<211> LENGTH: 25
<212> TYPE: DNA
<213> ORGANISM: Artificial sequence
<220> FEATURE:
<223> OTHER INFORMATION: Synthetic

<400> SEQUENCE: 6
gtacatttgc ctgccattgt gctgc                                       25

<210> SEQ ID NO 7
<211> LENGTH: 24
<212> TYPE: DNA

```
<213> ORGANISM: Artificial sequence
<220> FEATURE:
<223> OTHER INFORMATION: Synthetic

<400> SEQUENCE: 7
gagagcaccg tactggacca acac                                              24

<210> SEQ ID NO 8
<211> LENGTH: 26
<212> TYPE: DNA
<213> ORGANISM: Artificial sequence
<220> FEATURE:
<223> OTHER INFORMATION: Synthetic

<400> SEQUENCE: 8
gaccacactt tccataataa ggctcc                                            26
```